(12) United States Patent
Spenser et al.

(10) Patent No.: US 7,819,844 B2
(45) Date of Patent: Oct. 26, 2010

(54) GUIDEWIRE STOP

(75) Inventors: Benjamin Spenser, Hof Karmel (IL); Chen Barak, Shoham (IL); Ronen Neeman, Givaataim (IL); Gonen Somekh, Kerem Maharal (IL)

(73) Assignee: Gardia Medical Ltd., Caesarea (IL)

( * ) Notice: Subject to any disclaimer, the term of this patent is extended or adjusted under 35 U.S.C. 154(b) by 261 days.

(21) Appl. No.: 11/873,882

(22) Filed: Oct. 17, 2007

(65) Prior Publication Data

US 2009/0105653 A1 Apr. 23, 2009

(51) Int. Cl.
*A61M 5/178* (2006.01)
*A61M 29/00* (2006.01)

(52) U.S. Cl. .................. 604/165.02; 604/164.13; 606/200

(58) Field of Classification Search ........... 604/158, 604/164.01–164.04, 164.07, 164.12, 164.13, 604/165.01–165.03, 167.06; 606/200
See application file for complete search history.

(56) References Cited

U.S. PATENT DOCUMENTS

| | | | |
|---|---|---|---|
| 4,425,908 A | 1/1984 | Simon | |
| 5,741,270 A | 4/1998 | Hansen et al. | |
| 5,782,861 A * | 7/1998 | Cragg et al. | 606/216 |
| 5,848,964 A | 12/1998 | Samuels | |
| 5,984,950 A | 11/1999 | Cragg et al. | |
| 6,099,549 A | 8/2000 | Bosma et al. | |
| 6,179,859 B1 | 1/2001 | Bates et al. | |
| 6,254,525 B1 | 7/2001 | Reinhardt et al. | |
| 6,371,971 B1 | 4/2002 | Tsugita et al. | |
| 6,432,122 B1 | 8/2002 | Gilson et al. | |
| 6,537,295 B2 | 3/2003 | Petersen | |
| 6,562,058 B2 | 5/2003 | Seguin et al. | |
| 6,656,202 B2 | 12/2003 | Papp et al. | |
| 6,827,722 B1 | 12/2004 | Schoenefeld | |
| 2001/0041908 A1 | 11/2001 | Levinson et al. | |
| 2002/0062133 A1 | 5/2002 | Gilson et al. | |
| 2002/0082558 A1 | 6/2002 | Samson et al. | |
| 2002/0091407 A1 | 7/2002 | Zadno-Azozo et al. | |
| 2002/0091408 A1 | 7/2002 | Sutton | |
| 2002/0095174 A1 | 7/2002 | Tsugita et al. | |
| 2002/0138094 A1 | 9/2002 | Borillo et al. | |
| 2002/0151927 A1 | 10/2002 | Doiuk et al. | |

(Continued)

FOREIGN PATENT DOCUMENTS

DE 19846630 4/2000

(Continued)

OTHER PUBLICATIONS

Topol et al., "Recognition of the Importance of Embolization in Athereosclerotic Vascular Disease," Circulation, 101:570-580, (2000).

(Continued)

*Primary Examiner*—Nicholas D Lucchesi
*Assistant Examiner*—Nathan R Price
(74) *Attorney, Agent, or Firm*—Rissman Hendricks & Oliverio, LLP

(57) ABSTRACT

A guidewire stop is disclosed which can be positioned and frictionally locked to a bare guidewire at a user-defined location. The guidewire stop can be used to stop and/or lock a medical device, such as an embolic filter, at a treatment site inside a body lumen. The medical device may be attached to the guidewire stop.

23 Claims, 18 Drawing Sheets

U.S. PATENT DOCUMENTS

| | | |
|---|---|---|
| 2002/0165574 A1 | 11/2002 | Ressemann et al. |
| 2002/0165598 A1 | 11/2002 | Wahr et al. |
| 2002/0183782 A1 | 12/2002 | Tsugita et al. |
| 2003/0225435 A1 | 12/2003 | Hunter et al. |
| 2004/0098032 A1 | 5/2004 | Papp et al. |
| 2004/0102789 A1 | 5/2004 | Baughman |
| 2004/0199198 A1 | 10/2004 | Beulke et al. |
| 2006/0015139 A1 | 1/2006 | Tsugita et al. |
| 2006/0030876 A1* | 2/2006 | Peacock et al. .............. 606/200 |

FOREIGN PATENT DOCUMENTS

| | | |
|---|---|---|
| WO | WO 02/40090 | 5/2002 |
| WO | 2007035885 A2 | 3/2007 |

OTHER PUBLICATIONS

International Search Report for PCT Application No. PCT/IB2008/051155, dated Feb. 24, 2009.

* cited by examiner

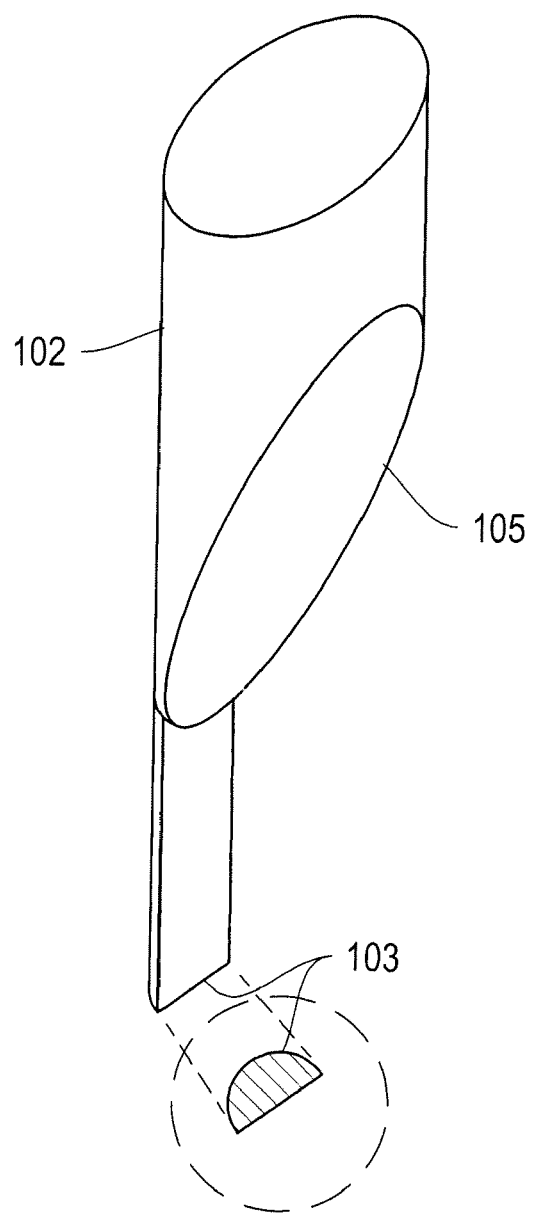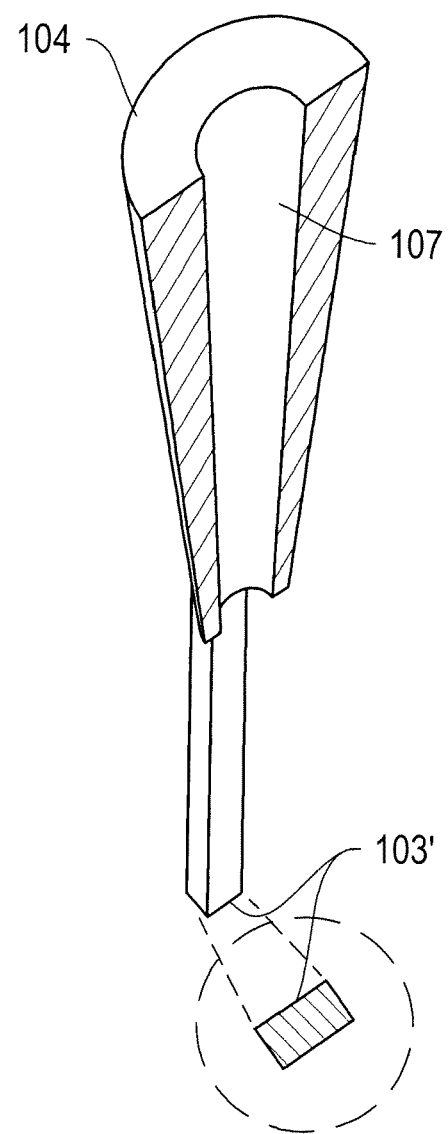
Fig. 10a
Fig. 10b

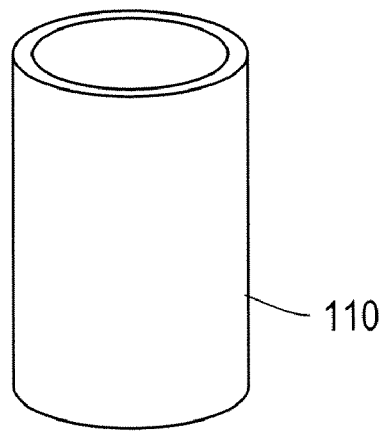
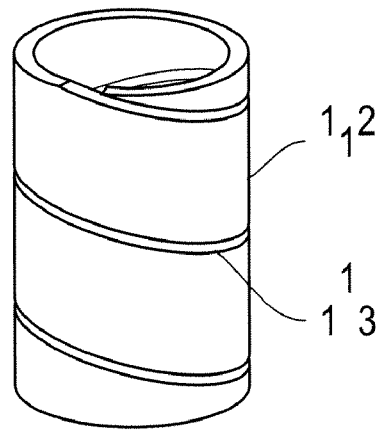
Fig. 11a          Fig. 11b
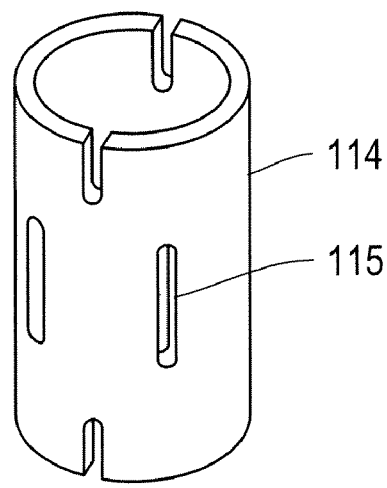
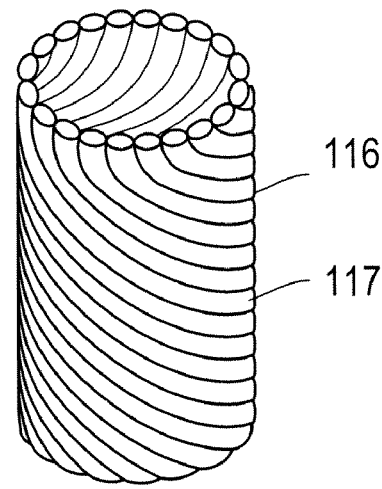
Fig. 11c          Fig. 11d
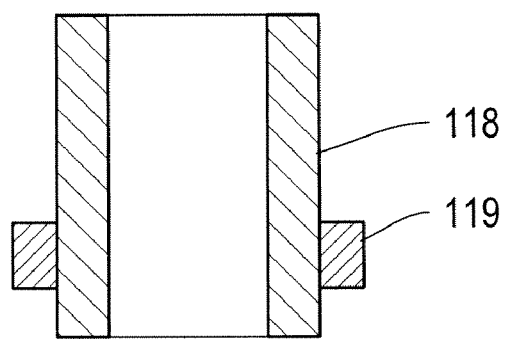
Fig. 11e

GUIDEWIRE STOP

FIELD OF THE INVENTION

The present invention relates generally to the field of medical procedures which employ a guidewire. In particular, the present invention relates to an actuatable guidewire stop capable of stopping and/or locking a medical device on a guidewire at a location in the body lumen defined by the user.

BACKGROUND OF THE INVENTION

Transcatheter procedures are employed in increasing numbers for opening stenosed or occluded blood vessels in patients caused by deposits of plaque or other materials on the walls of the blood vessels. Such minimally invasive procedures have proven to be advantageous compared to traditional surgical procedures, such as open heart surgery. Stenosis in arteries and other blood vessels can be treated by permanently or temporarily introducing a stent into the stenosed region to open the lumen of the vessel.

However, embolic material may be released into the blood stream during implantation of a stent or another prosthetic device, placing the patient at great risk. Embolic material formed of calcium deposits, intimal debris, pieces of artheromatous plaque and/or thrombi has the potential of migrating downstream and causing distal tissue damage, for example stroke or myocardial infarction (see Topol, E. J. and Yadov, J. S., "Recognition of the Importance of Embolization in Athereosclerotic Vascular Disease", Circulation 2000, 101: 570). Embolic material which can potentially damage the distal tissue is often released during vascular intervention procedures, such as stenting of an artheromatous region.

To alleviate this problem, an embolic filter may be advanced to a site distal to the treatment site to filter and capture undesired embolic material from the blood. The filter is typically formed from a mesh material mounted on an expansion frame adapted to open from a contracted (or collapsed) configuration to a deployed (or open) configuration. The filter is typically inserted over or together with a guidewire using a delivery catheter. Following the treatment procedure, the filter is collapsed and removed from the body over the guidewire or together with the guidewire. Additional treatment devices, such as balloons and stents, can be inserted and removed via the same guidewire.

The filter should be positioned at a location as close as possible distal of the treatment site to ensure that most or all of the embolic debris is trapped by the filter. On the other hand, the guidewire should extend as far as possible into the body lumen to stabilize the treatment site. It is extremely difficult to achieve both these objectives simultaneously when using a built-in filter stop, because accurate placement of the stop relative to the treatment site by fluoroscopic observation is very difficult.

Therefore, there is a need for a guidewire stop capable of being stopped/locked on a bare guidewire, i.e. a guidewire section devoid of a preformed or fixedly attached stop. There is also a need for an intravascular treatment device capable of being stopped and/or locked on the guidewire at any user-selectable position following deployment of the treatment device in the body lumen.

SUMMARY OF THE INVENTION

The present invention relates to a user-actuatable guidewire stop which can be used to stop and/or lock a medical device on a guidewire following advancement of the guidewire through a body lumen. It will be appreciated that this provides the user with a significant advantage, since instead of the medical device being preassembled onto the guidewire as is known in the art, the present invention allows for the user to determine precisely where the medical device is to be placed after the guidewire has been introduced into the body. This is of particular significance, especially when dealing with occluded blood vessels where it is crucial to place an embolic filter at a location where virtually all embolic debris will be trapped.

The term "guidewire" as employed in the present disclosure is intended to refer to any elongated member used to facilitate the advancement of other elements through body lumens. The guidewire may be any standard, non-dedicated guidewire known in the art. There is no need for dedicated guidewire. After the guidewire stop is locked onto the guidewire, the proximal length of the guidewire is available for use for any other purpose or with additional medical devices.

According to one aspect of the invention, an actuatable guidewire stop configured to limit movement of an intravascular device relative to a guidewire includes a locking tube disposed about the guidewire and having a locked configuration, wherein the locking tube is prevented from movement relative to the guidewire, and an unlocked configuration, wherein the locking tube is moveable relative to the guidewire. The guidewire stop further includes a locking element disposed between the guidewire and the locking tube and in frictional engagement with at least the guidewire in the locked configuration, and an actuator operatively coupled to the locking element for switching the locking tube from the unlocked configuration to the locked configuration.

According to another aspect of the invention, an intravascular treatment device has a guidewire stop configured to limit movement of an intravascular device relative to a guidewire. The guidewire stop includes a locking tube disposed about the guidewire and having a locked configuration, wherein the locking tube is prevented from movement relative to the guidewire, and an unlocked configuration, wherein the locking tube is moveable relative to the guidewire. The guidewire stop further includes a locking element disposed between the guidewire and the locking tube and in frictional engagement with at least the guidewire in the locked configuration, and an actuator operatively coupled to the locking element for switching the locking tube from the unlocked configuration to the locked configuration.

According to yet another aspect of the invention, a method is disclosed for securing a guidewire stop along a length of a guidewire having a substantially uniform diameter. The guidewire stop includes a locking tube disposed about the guidewire, a locking element disposed between the guidewire and the locking tube, and an actuator operatively coupled to the locking element. The method includes the steps of advancing the guidewire stop with a catheter along the guidewire to a desired location, actuating the actuator so as to draw the locking element substantially into the locking tube, thereby moving the locking element from an unlocked configuration to a locked configuration, detaching the actuator from the locking element, and withdrawing the actuator in a proximal direction of the guidewire.

Embodiments of the invention may include one or more of the following features. The locking tube may be made of a resilient, yielding or springy material and may include structural features, such as a grooved, spiral and multifilar structure. The locking tube may be formed, for example, from nitinol.

According to embodiments of the invention, the locking element may be a tapered member with, for example, at least one friction-generating surface providing the frictional engagement with the guidewire and/or the locking tube. The tapered member may include a spring, for example a helical spring. The tapered member may be configured as a wedge and may optionally include a recess adapted to receive the guidewire. Such arrangement may reduce the overall diameter of the locking tube for the guidewire stop.

According to other embodiments of the invention, the locking element may include an opening along a central axis through which the guidewire passes. The locking element may then be urged inwardly towards and in engagement with the guidewire when the locking element is drawn into the locking tube through actuation of the actuator. In an alternative embodiment, the locking element may be prebiased to engage the guidewire and disengage from the guidewire when the locking element is pulled into the locking tube.

In one embodiment of the invention, the locking element may include one or more jaws or prongs, whereby the jaws or prongs are urged inwardly for engagement with the guidewire when the locking element is drawn into the locking tube through actuation of an actuator. The jaws or prongs may have one or more teeth to increase friction on the guidewire.

In embodiments of the invention, the actuator may be implemented as a pulling wire with a rated break point, which may advantageously be placed close to the locking element. The locking element and the actuator may be formed as a single integral unit.

In another embodiment of the invention, the actuator may be operatively coupled to the locking element by a separable screw connection. In yet another embodiment, the locking element may be moved into frictional engagement with at least the guidewire by a rotary movement of the actuator. For example, the locking tube may be threaded in the locking element with an actuator having an actuation tube adapted for rotationally coupling to the locking element.

According to another embodiment, the actuator may engage with an annular groove disposed on an end of the locking element and disengage from the annular groove when the locking tube is in the locked configuration, wherein the annular groove is located outside the locking tube.

With the disclosed embodiments, the actuator may be disconnected from the locking element through user activation and subsequently withdrawn from the body lumen. The pulling wire generally separates from the locking element when a pulling force applied longitudinally in a proximal direction exceeds a predetermined value.

Further according to embodiments of the present invention, the guidewire stop is advanced using a catheter.

These and other features and advantages of the present invention will become more readily appreciated from the detailed description of the invention that follows.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

FIGS. 1a-1c show schematically an exemplary embodiment of a guidewire stop according to the invention, wherein FIG. 1a shows the guidewire stop an unlocked configuration, FIG. 1b in a locked configuration without a guidewire, and FIG. 1c in a locked configuration gripping the guidewire;

FIGS. 10a and 10b show schematically other exemplary embodiments of wedge-shaped locking element according to the invention;

FIGS. 11a-11e represent schematic views of various embodiments of locking tubes according to the invention;

DETAILED DESCRIPTION OF CERTAIN ILLUSTRATED EMBODIMENTS

The disclosed devices are directed to guidewire stops (or locks) capable of locking on a bare guidewire, i.e., a guidewire that does not include stops or locks applied to or formed on the guidewire prior to insertion of the guidewire into the body lumen. The approach allows the clinician to use in conjunction with a specific medical device any guidewire suitable for a procedure regardless of the design of the guidewire or its intended use.

The disclosed guidewire stops share as a common characteristic an outer locking tube, a locking element disposed at least partially inside the locking tube, and a user-activated actuator which allows the user to place the guidewire stop, with or without an attached medical device, such as an embolic protection filter, at any desired location along the guidewire. Placement of the guidewire stop can be monitored in a conventional manner by fluoroscopic observation using radiopaque markers.

Figure 1A:
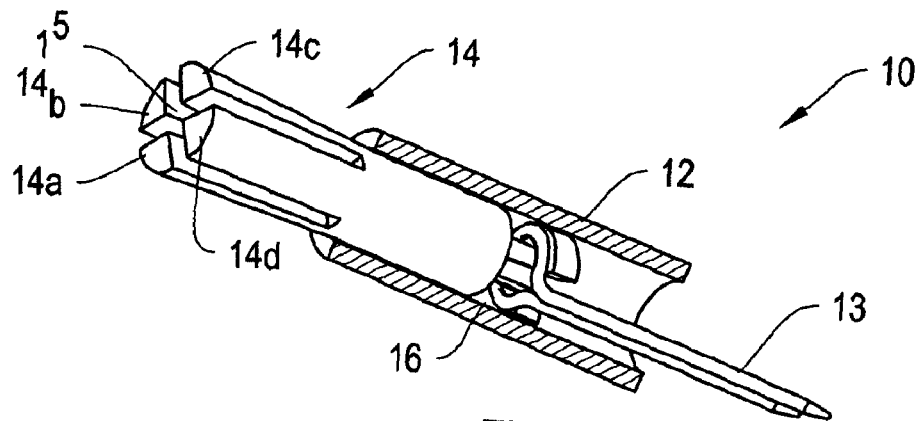
Figure 1B:
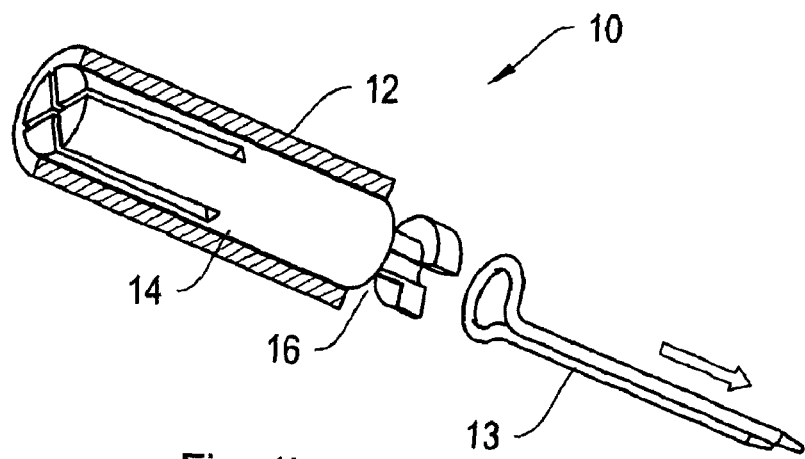
Figure 1C:
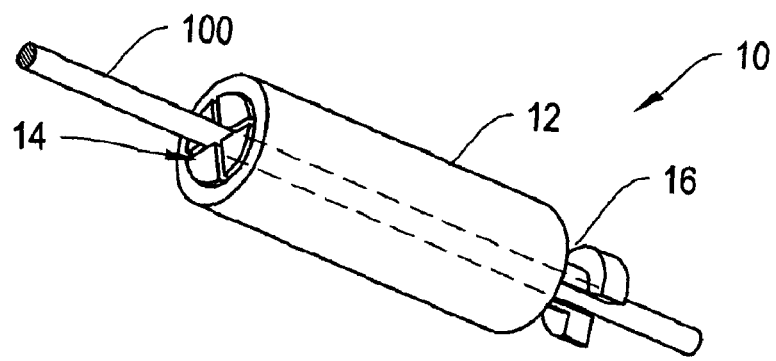

According to one exemplary embodiment of the invention shown schematically in FIGS. 1a, 1b, and 1c, a guidewire stop 10 includes a locking tube 12 and a locking element 14, shown here as having a generally cylindrical shape. In the illustrated embodiment, locking element 14 has four prongs 14a, 14b, 14c, 14d which are biased in an open position about an opening 15 adapted to receive a guidewire. The base of locking element 14 includes an annular groove 16 adapted to engage with an actuator 13, shown here as a pulling wire. Pulling wire 13 is held captive in the annular groove 16 when inside the locking tube 12. As shown in FIG. 1b, when the locking element 14 is drawn into locking tube 12, prongs 14a, 14b, 14c, 14d are urged inwardly, and the pulling wire 13 exits from the locking tube, allowing the pulling wire 13 to disengage from the annular groove 16 and being pulled out in the proximal direction. When used with a guidewire 100, as illustrated in FIG. 1c, the four prongs 14a, 14b, 14c, 14d of the locking element 14 grip the guidewire and lock the guidewire stop 10 on guidewire 100.

In operation, the user first pulls on pulling wire 13 to cause locking element 14 to move downward into locking tube 12 and to lock locking tube 12 onto guidewire 100. Continued pulling on wire 13 causes pulling wire 13 to disengage from annular groove 16, so that the pulling wire 13 can be removed from the site of the medical procedure.

Figure 3:
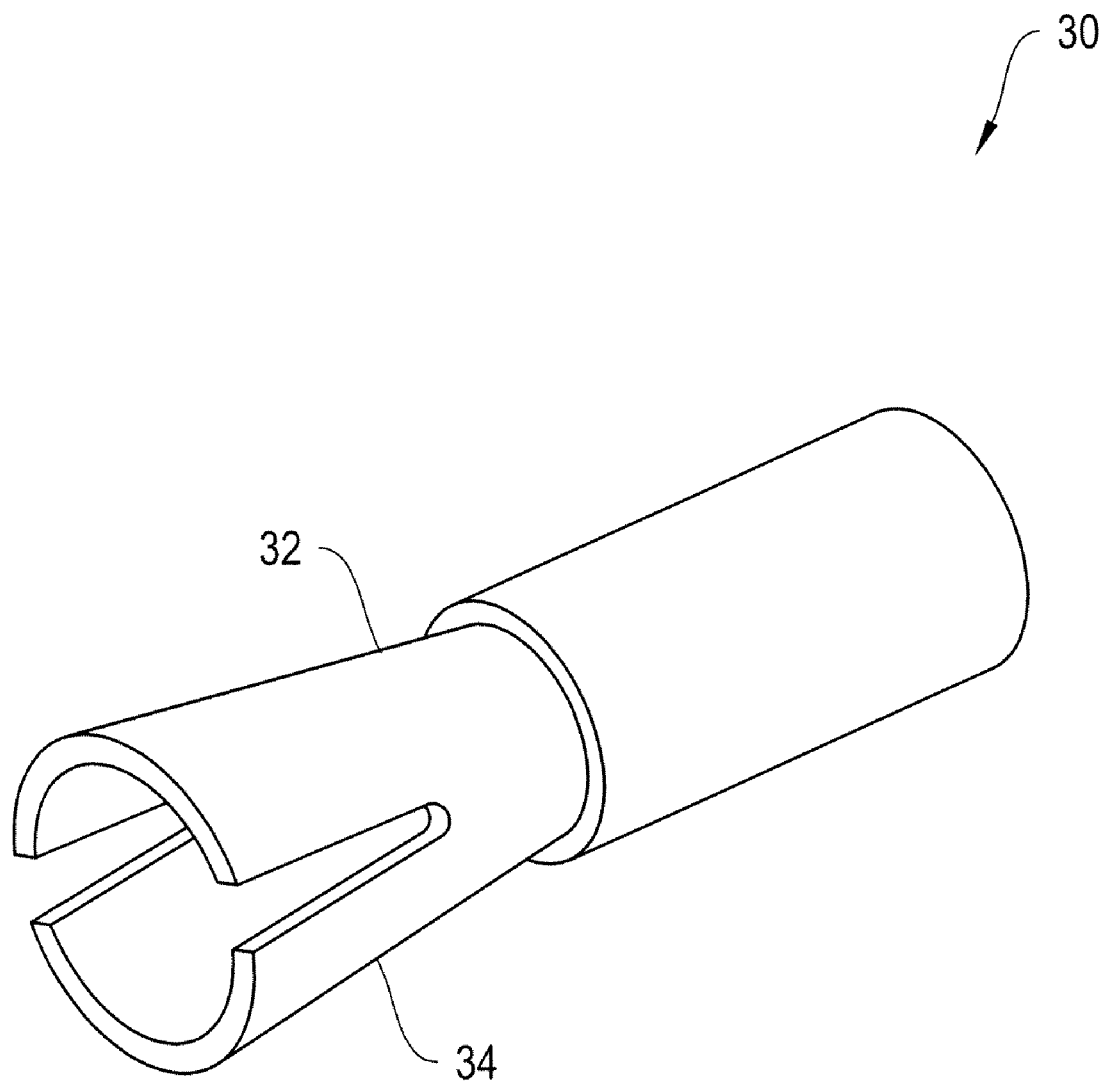
FIG. 3 shows schematically another exemplary embodiment of a guidewire stop according to the invention.

Turning now to FIG. 3, the depicted exemplary embodiment of a guidewire stop 30 according to the invention has two prongs 32, 34 instead of the four prongs of FIGS. 1a-1c. In all other aspects, the operation of the stop 30 is identical to that of stop 10. The actuator has been omitted so as not to obscure the clarity of the drawing.

Figure 2A:
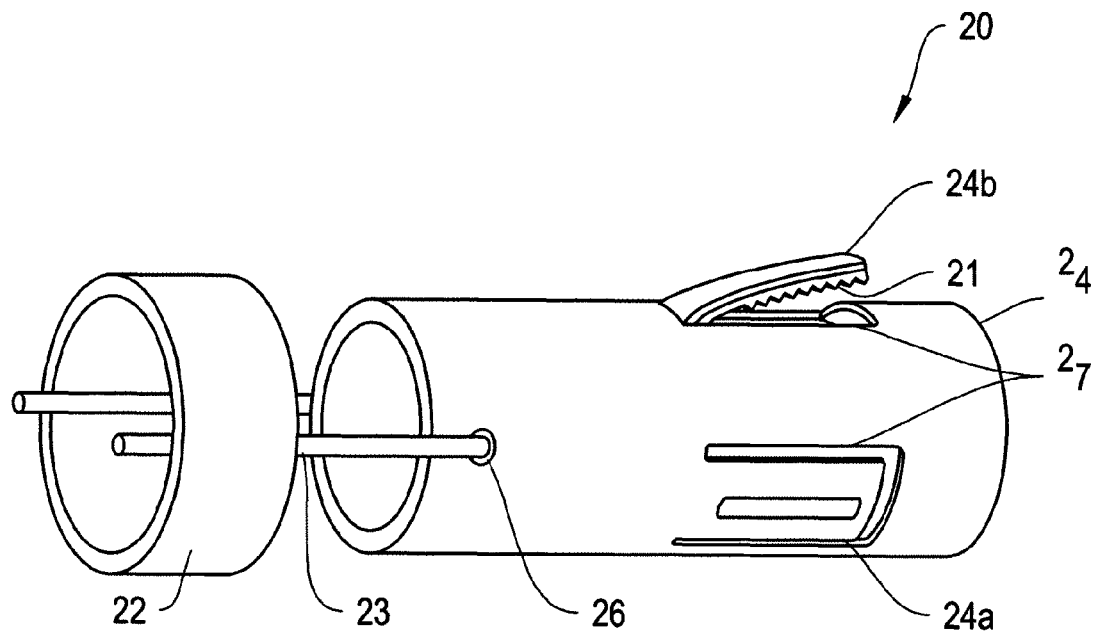
FIGS. 2a and 2b show schematically other exemplary embodiments of a guidewire stop according to the invention.
Figure 2B:
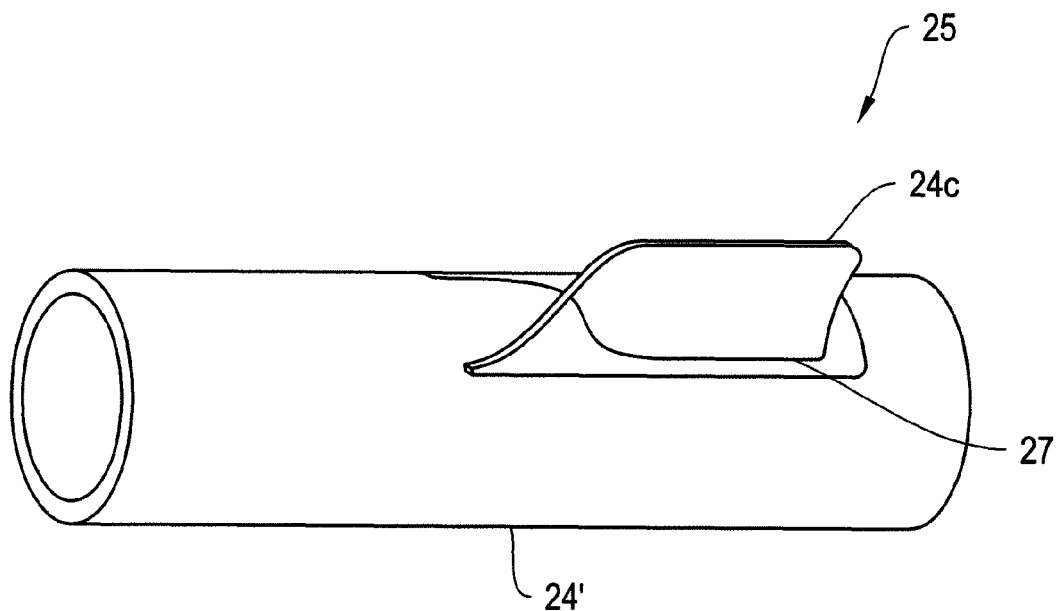

FIGS. 2a and 2b show other embodiments of locking elements operating according to the same principle as the locking element 10 of FIGS. 1a-1c. Guidewire stop 20 depicted in FIG. 2a includes a locking element 24 with a plurality of protruding elements 24a, 24b formed in windows 27. Locking element 24 can be made from a tube, with the prongs machined from the tube wall, for example, by laser cutting. Different embodiments may have different numbers of protruding elements 24a, 24b (for example, between one and four, or even more). In some embodiments, protruding elements 24a, 24b, as well as the prongs 14a-14d in FIG. 1a, may include one or more teeth 21 to enhance frictional engagement on the guidewire (not shown). In another exemplary embodiment of a locking element 25 illustrated in FIG. 2b, the protruding element 24c is shown as having a twisted configuration with a sharp edge 27. To lock the protruding elements 24a, 24b, as well as protruding element 24c on a guidewire, the respective locking element 20, 25 is pulled into locking tube 22 (omitted from FIG. 2b) by actuator implemented as a pulling wire 23. As seen in FIGS. 2a and 2b, the protruding elements 24a, 24b, 24c are prebiased in the unlocked position and closed by being drawn into the locking tube 22.

The pulling wire 23 in FIG. 2a is illustrated as having an enlarged end 26 which engages in a recess in the wall of locking element 20 (and likewise 25, where the actuator/pulling wire has been omitted from the figure). In operation, the user pulls pulling wire 23 proximally to cause locking element 24, 24' to be drawn into locking tube 22, thereby locking the locking element 24, 24' onto a guidewire. The user then continues to pull on pulling wire 23, so that enlarged end 26 of pulling wire 23 disengages from the recess in locking element and can be withdrawn. It will be appreciated that the depicted user-activated actuators are only exemplary, and that other actuators may be employed in these and other embodiments illustrated in this disclosure. Likewise, is noted that certain features of specific embodiments described throughout this disclosure may be combined with features of other embodiments, while still falling within the scope of the present invention, as would be readily obvious to one skilled in the art.

Figure 4A:
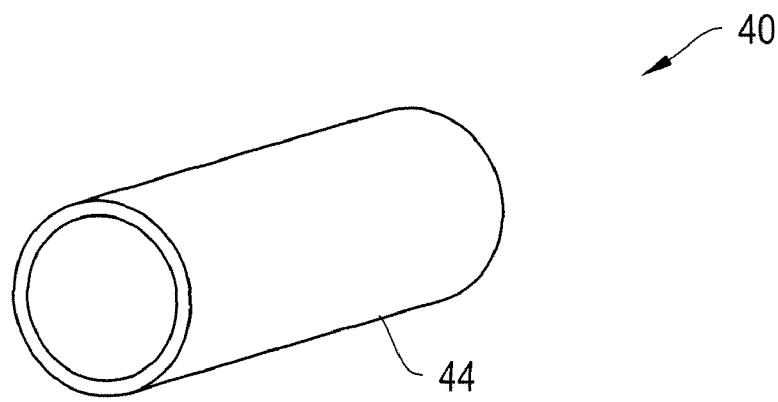
FIGS. 4a-4c show schematically a locking element and a locking tube of a guidewire stop according to another embodiment of the invention.
Figure 4B:
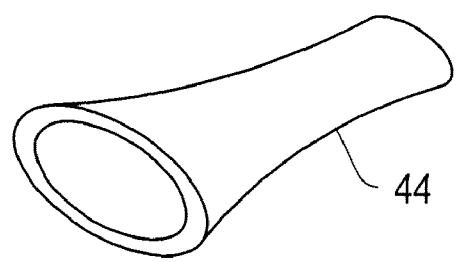
Figure 4C:
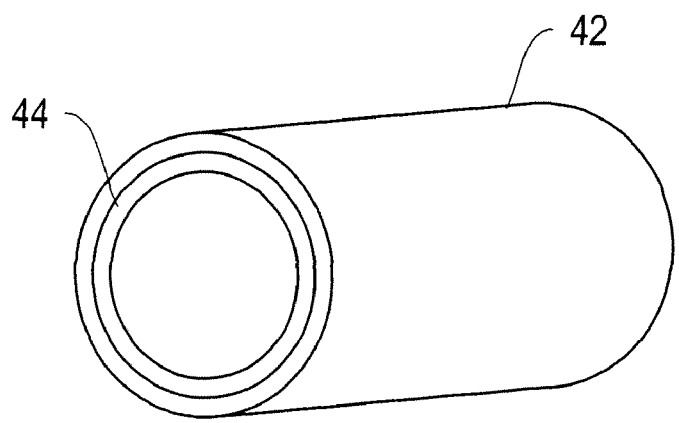

FIGS. 4a-4c show another exemplary embodiment of a guidewire stop 40, where a locking element 44 is shaped (for example, by using a shape-memory alloy) to close around a guidewire (not shown) in an unrestrained configuration, as depicted in FIG. 4b. The locking element 44 cooperates with a locking tube 42 (FIG. 4c) and is forced into an open configuration (FIG. 4a) when drawn into the locking tube 42.

Figure 5A:
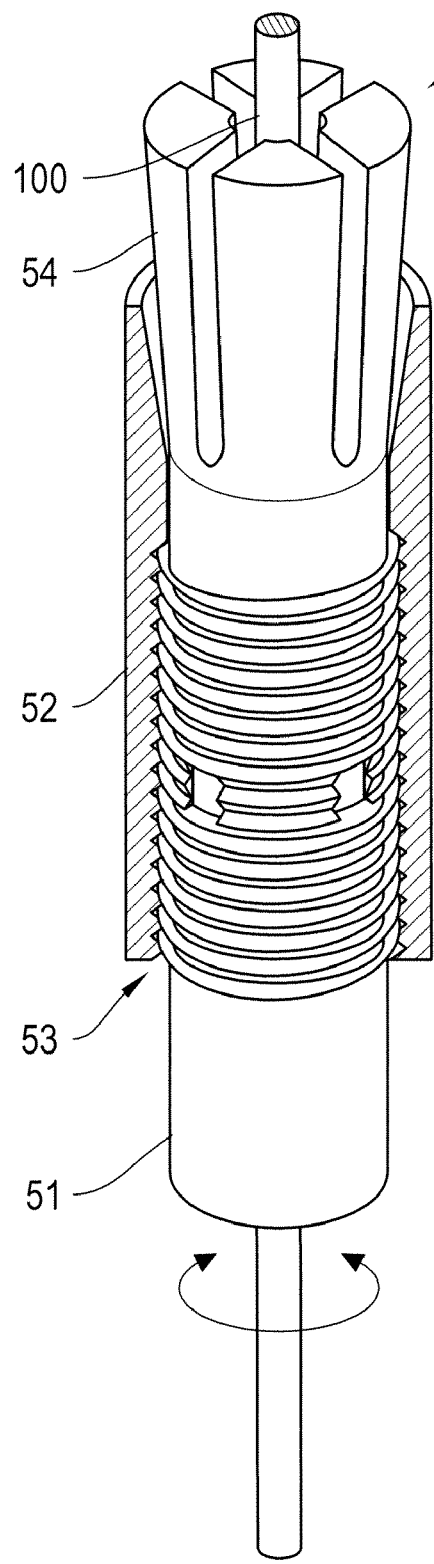
FIGS. 5a and 5b show schematically another exemplary embodiment, unlocked and locked, respectively, of a guidewire stop according to the invention.
Figure 5B:
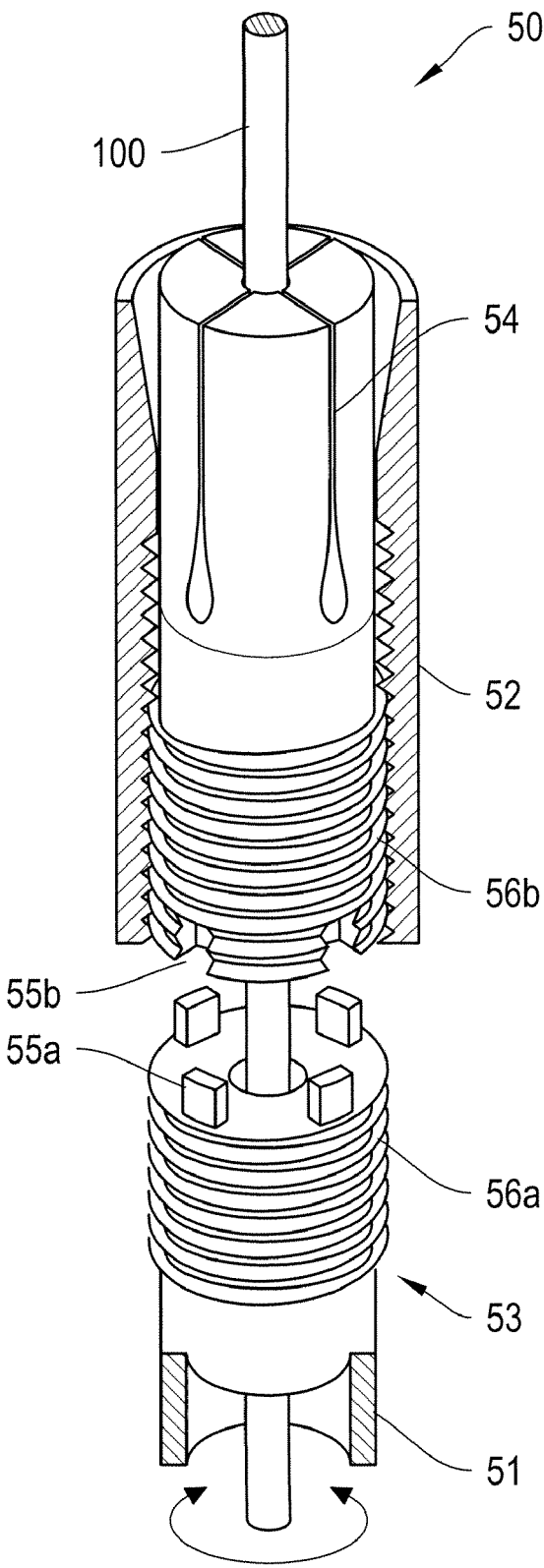

Turning now to FIGS. 5a and 5b, in another exemplary locking element embodiment of a guidewire stop 50, locking element 54 is moved into locking tube 52 by rotating a screw actuator 53. The actuator 53 may be constructed of an actuation tube 51 with a threaded end section 56a having coupling projections 55a adapted to engage with corresponding coupling recesses 55b formed on the proximal threaded end section 56b of locking element 54. When guidewire stop 50 is initially assembled and in an open configuration (FIG. 5a), both threaded end sections 56a and 56b are screwed into the locking tube 52, and thus held firmly in place. When the guidewire stop 50 is operated to engage guidewire 100, actuation tube 51 is rotated, causing the two end sections 56a and 56b to move downward in unison, thereby drawing locking element 54 into locking tube 52 and locking the locking element 54 on guidewire 100. Actuator 53 disengages from the threaded portion of locking tube 52 when the locking element 54 is fully drawn into the locking tube 52, as indicated in FIG. 5b and can now be withdrawn proximally from the body lumen.

Figures 6A, 6B:
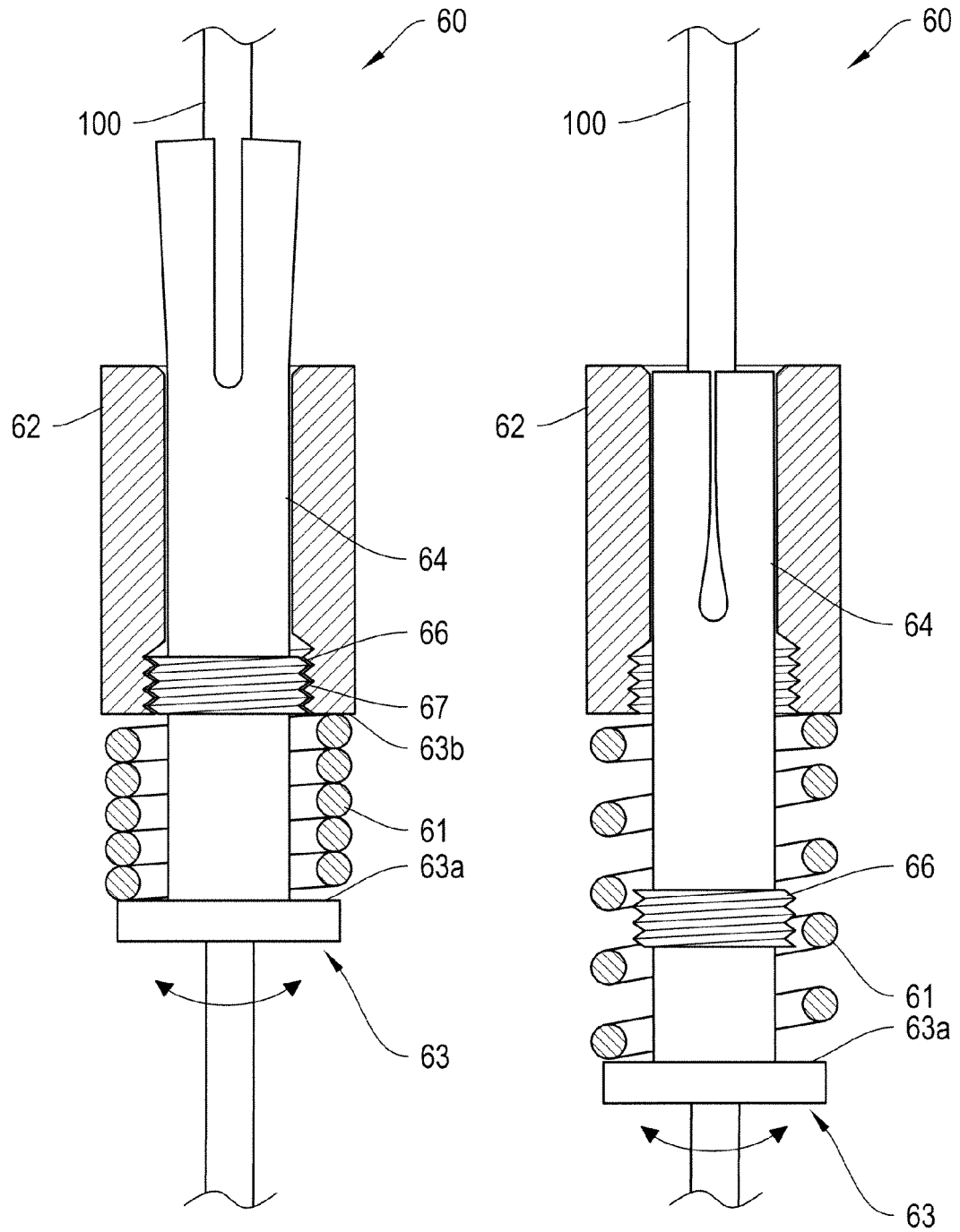
FIGS. 6a and 6b show schematically another exemplary embodiment, unlocked and locked, respectively, of a guidewire stop according to the invention.

FIGS. 6a and 6b show another exemplary embodiment of a guidewire stop 60 actuated by a rotary motion. However, unlike in the embodiment of FIGS. 5a and 5b, the locking element 64 does not necessarily rotate inside locking tube 62 when the actuator 63 rotates. Instead, locking element 64 is drawn into locking tube 62 by a biased spring 61 supported with one end on a shoulder 63a of actuator 63 and with the other end on an end face 63b of locking tube 62. Locking tube 62 has an interior threaded portion 67 engaging with an exterior thread 66 disposed on actuator 63. In the open configuration of locking element 64, i.e., when locking element 64 does not grip the guidewire 100, the actuator 63 is screwed into locking tube 62 compressing spring 61. When the actuator 63 is unscrewed, the threaded portion 66 moves out of the locking tube 62 releasing spring 61 which draws locking element 64 into locking tube 62 and locks locking element 64 around guidewire 100.

It is appreciated by those skilled in the relevant art that other types of user-actuating means could be used in the context of the present invention. For example, an actuator may include an electromagnetically actuated coil. Other possible user-actuating means will be described further below. The user-activated actuator in cooperation with the locking element should produce the highest possible holding force on the guidewire a ratio with a reasonably attainable actuation force.

Figure 7A:
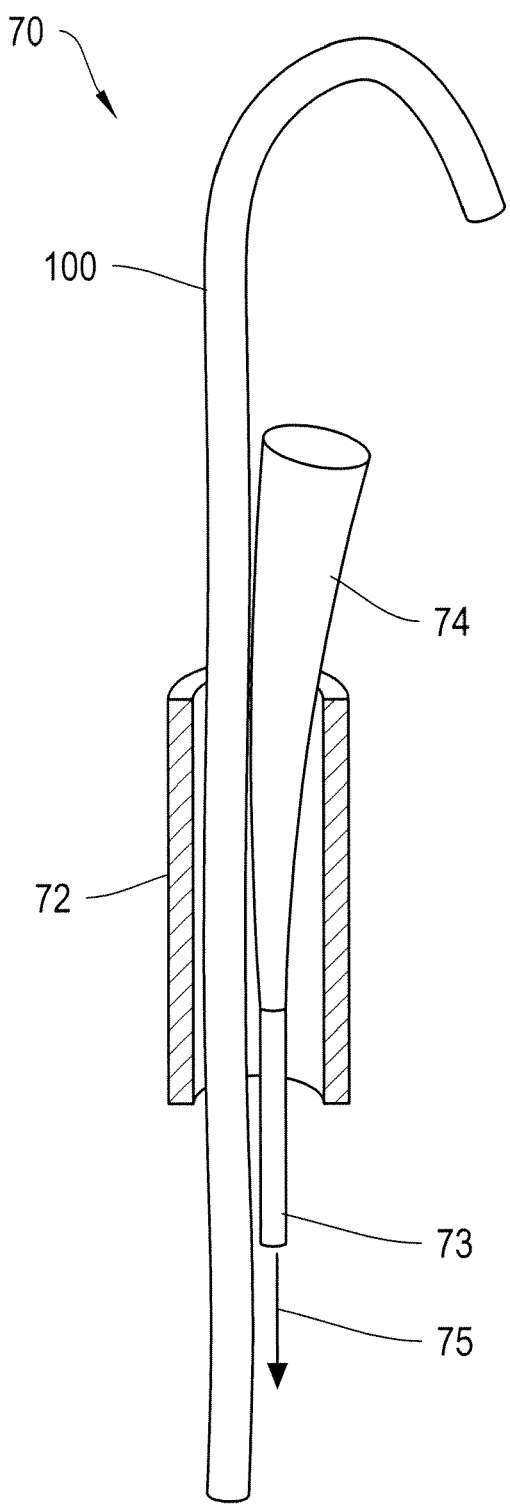
FIGS. 7a and 7b show schematically an exemplary embodiment of a tapered member a guidewire stop, unlocked and locked, respectively, according to the invention.
Figure 7B:
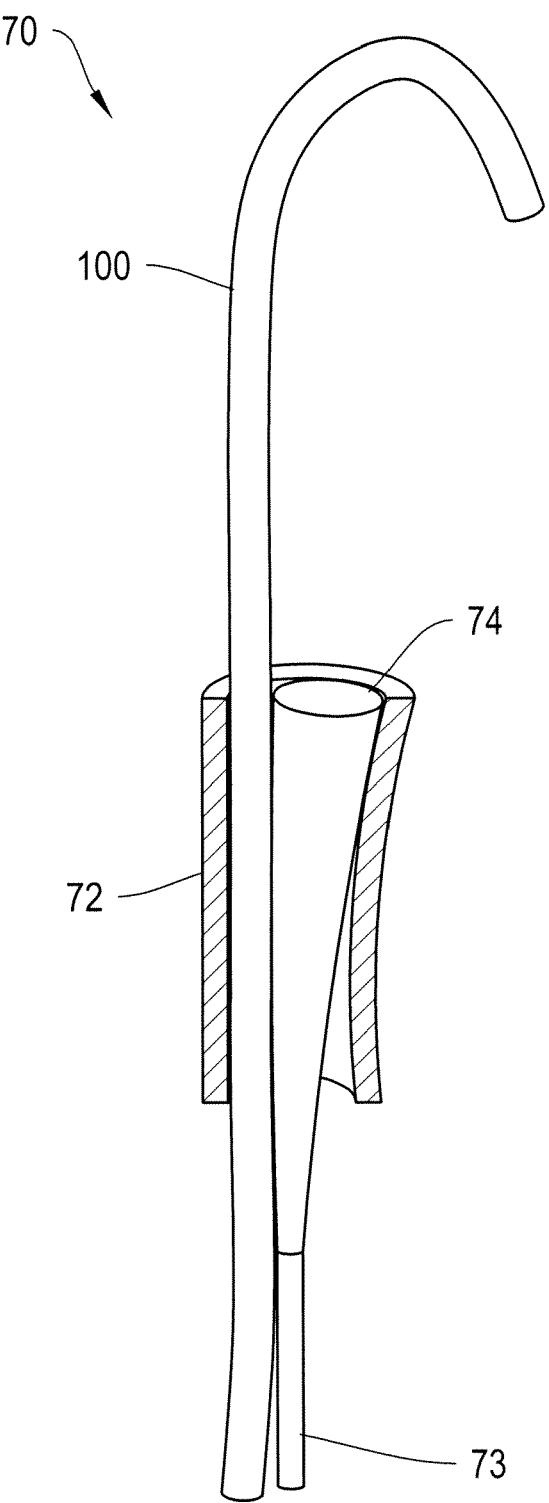

Another exemplary embodiment of a guidewire stop 70 with a different type of locking element 74 is illustrated in FIGS. 7a and 7b, showing the guidewire stop 70 in an unlocked configuration (FIG. 7a) and in a locked configuration (FIG. 7b). In this embodiment, the locking element 74 is implemented as a tapered (wedge-shaped) element 74.

The wedge-shaped element 74 is drawn into locking tube 72 by moving an actuator 73, here a pulling wire 73, in the proximal direction, as indicated by arrow 75. The wedge-shaped element 74 then becomes wedged between guidewire 100 and locking tube 72, thus locking the locking tube 72 to guidewire 100 by friction.

Advantageously, locking tube 72 may be formed from a springy or yielding material to allow for slight deformation or expansion of locking tube 72 when the wedge-shaped element 74 is drawn into the locking tube 72, as indicated in FIG. 7b. This allows the element 74 to be more securely locked on guidewire 100. The locking tube 72 may be formed, for example, from stainless steel, nitinol, plastic, or any other material exhibiting an appropriate degree of springiness or elasticity. Various designs of locking tubes will be described in more detail below with reference to FIGS. 11a-11e.

Figure 8A:
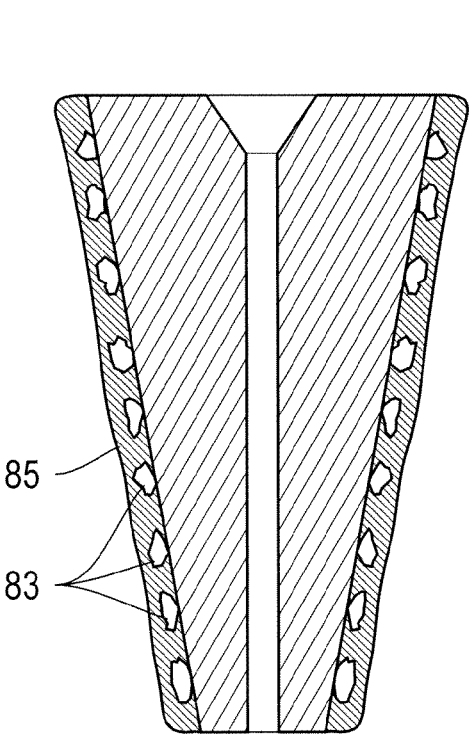
FIGS. 8a and 8b show schematically an exemplary embodiment of a wedge-shaped locking element according to the invention.
Figure 8B:
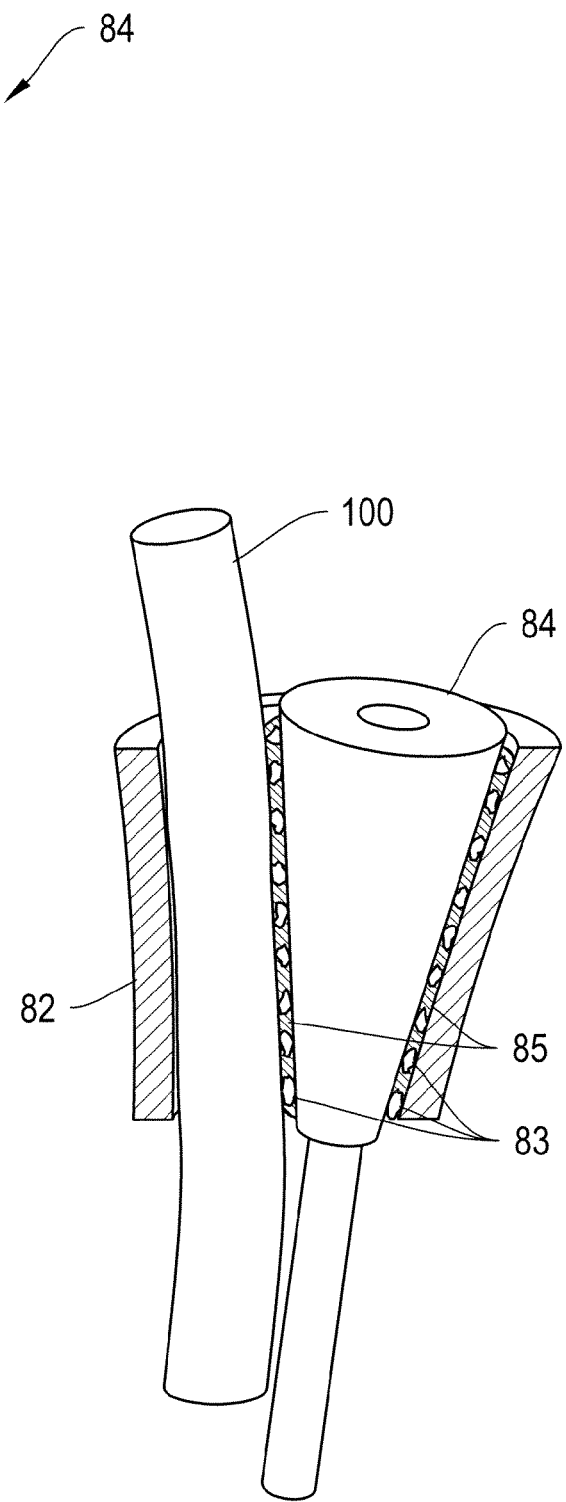

Frictional engagement of the wedge-shaped element 74 of FIGS. 7a and 7b on the guidewire 100 can be improved by providing the surface of a tapered or wedge-shaped locking element 84 illustrated in FIGS. 8a and 8b with a friction-generating component 83 or by roughening the surface. In some exemplary embodiments, for example glass particles, diamond dust, silica, carbon, or any suitable abrasive powder, can be impregnated on or embedded in the surface of locking element 84. Additionally, the surface of locking element 84 may be provided with a surface coating 85, such as a gel composition, PTFE, or hydrophilic coating, or any other suitable lubricant, to enable the wedge member 84 to slide into place with minimal friction, before locking on guidewire 100. As locking element 84 moves into locking tube 82, the coating 85 is redistributed, as illustrated in FIG. 8b, thereby exposing the friction generating component 83 which then contacts guidewire 100 and locking tube 82.

Figure 9A:
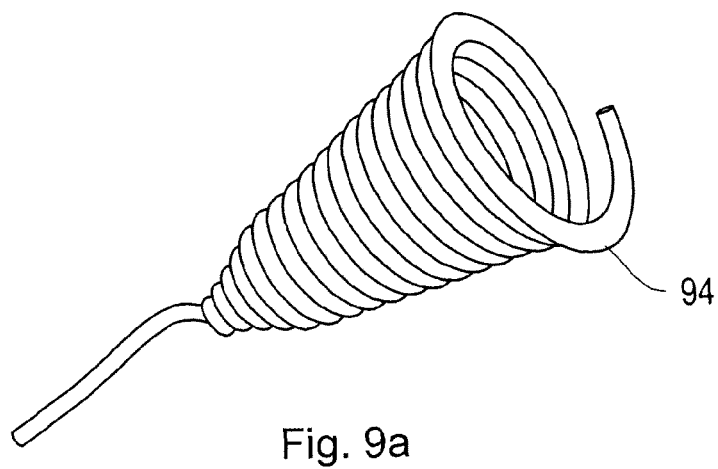
FIGS. 9a, 9b, and 9c show schematically an exemplary embodiment of a helical locking element (a) in an unlocked (b) position and a locked (c) position on a guidewire, according to the invention.
Figures 9B, 9C:
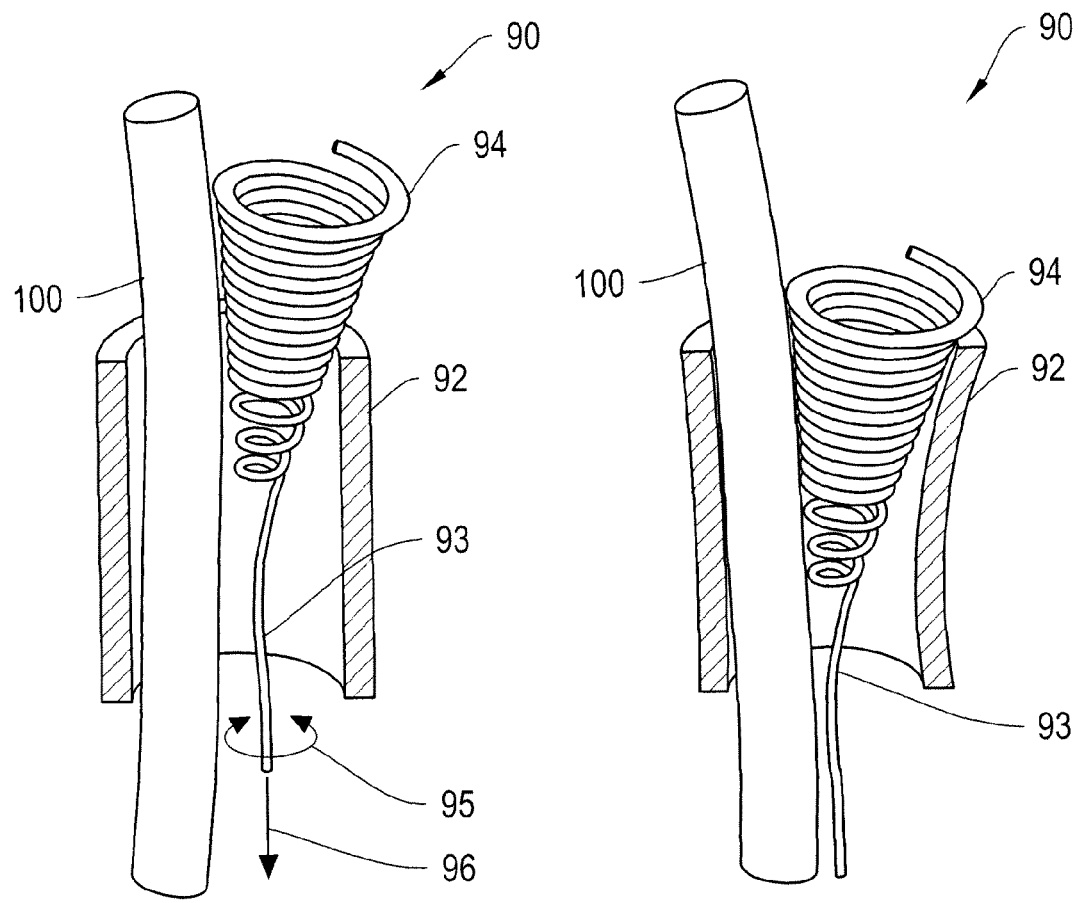

Turning now to FIGS. 9a, 9b, and 9c, in another embodiment of a guidewire stop 90 with a tapered locking element, the locking element 94 is implemented as a conical helical spring 94. To move the spring 94 into locking tube 92, the spring 94 can be rotated with actuator 93 clockwise in a direction indicated by arrow 95 and/or pulled proximally in the direction of arrow 96. Alternatively, a simple pulling motion on pulling wire 93 may be sufficient to draw spring 94 into the space between the guidewire 100 and the locking tube 92. As also indicated in FIG. 9c, locking tube 92 may slightly expand to accommodate spring 94 and thereby bias the spring 90 against guidewire 100.

FIGS. 10a and 10b illustrate other exemplary embodiments of wedge-shaped locking elements. The wedge member 102 in FIG. 10a has a planar locking surface 105 with a slope angle commensurate with the desired actuation force required to securely lock the wedge member in place between the locking tube and the guidewire (for example, when used with the embodiment shown in FIGS. 7a and 7b). The pulling wire 103 in FIG. 10a is shown as having a semicircular cross section (see insert) so as to better accommodate the pulling wire 103 together with the guidewire in a round delivery catheter.

It will be appreciated that the wedge-shaped element may have other suitable designs which effectively lock the element in place in between the locking tube and the guidewire. For example, the wedge-shaped element may have a round or square cross section.

Figure 10C:
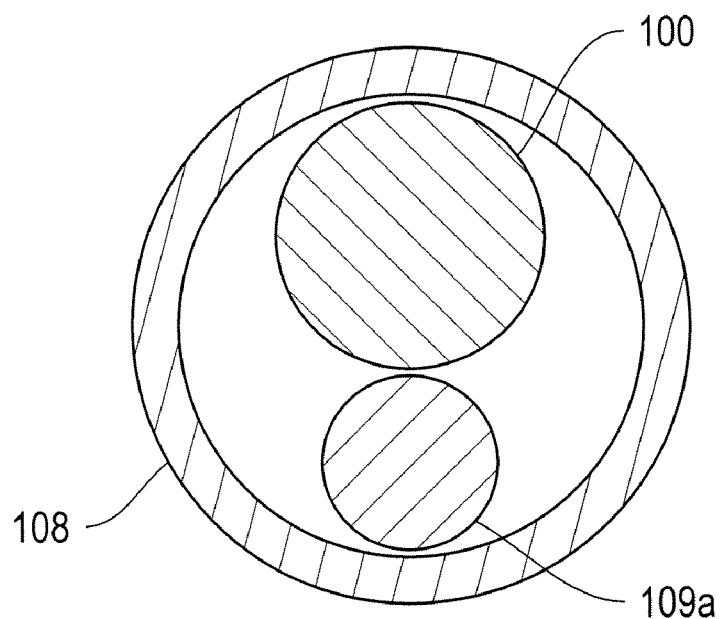
FIGS. 10c and 10d represent schematic cross-sectional views of a pulling wire cooperating with a guidewire, according to another embodiment of the invention.
Figure 10D:
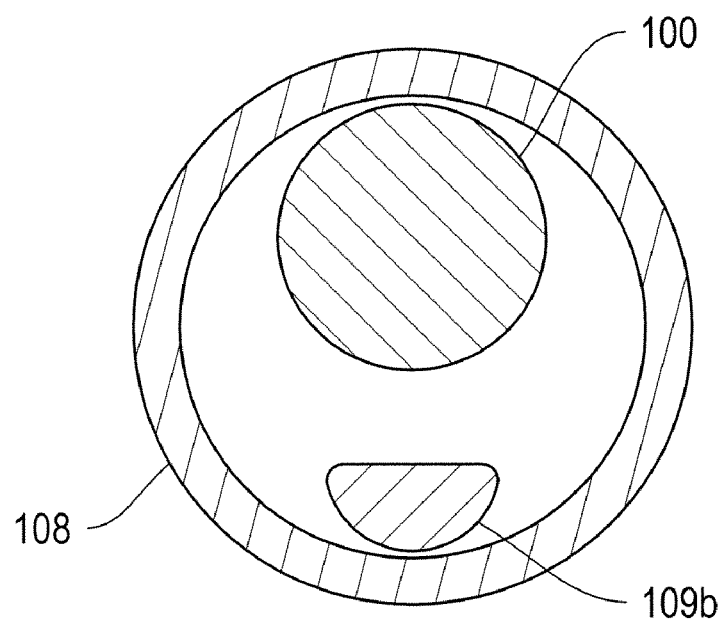

In the exemplary embodiment illustrated in FIG. 10b, the wedge-shaped element 104 has a tapered arcuate cross section with a longitudinal channel 107 configured for passage of a guidewire (not shown). This design enables the lock to be advanced using a locking tube or delivery catheter with a smaller diameter. The pulling wire 103' in FIG. 10b is shown with a rectangular cross-section (see insert), also for the purpose of reducing the space requirement for the pulling wire. The spatial arrangement of a round pulling wire 109a and of a flat or curved pulling wire 109b together with guidewire 100 in a locking tube 108 (or a delivery catheter) is illustrated in FIGS. 10c and 10d. It will be understood that such variations in the shape of the pulling wire are only exemplary and that other shapes may be employed capable of transmitting a large enough actuation force to the guidewire stop.

As mentioned above, the locking tubes employed with the aforedescribed guidewire stops of the invention may advantageously have a certain built-in springiness or resiliency. FIGS. 11a to 11e illustrate a number of exemplary embodiments for resilient locking tubes. The locking tube 118 depicted in FIG. 11a is tubular and may be made of a yielding composite material, such as Nitinol. The locking tube 112 depicted in FIG. 11b is tubular with a spiral groove 114 for adjusting the flexibility of locking tube 112. The flexibility of locking tube 114 depicted in FIG. 11c is increased by arranging a plurality of lengthwise grooves 116 in a tube. In some embodiments, the grooves 114 can be wide enough to snatch the guidewire. In another embodiment depicted in FIG. 10d, the locking tube 116 may be constructed as a multi-filamentary tube formed of a plurality of smaller springy elements 117. In another embodiment, the flexibility of locking tube 118 may be varied in a longitudinal direction by applying to or forming in the wall of the locking tube 118 a rigid constraining ring 119 (or alternatively a section with greater wall thickness). Constraining ring 119 inhibits locking tube 118 from yielding at a point where ring 119 is placed, thereby preventing the locking element (not shown) from being drawn further into the locking tube 118 after the locking element is seated in locking tube 118.

As discussed briefly before, the actuator is generally removed proximally after the locking element is locked to the guidewire. When using a pulling wire, locking element is first drawn between locking tube and guidewire, whereafter the pulling wire is severed at a predetermined location on the pulling wire, in general close to the proximal end of the locking element.

Figure 12A:
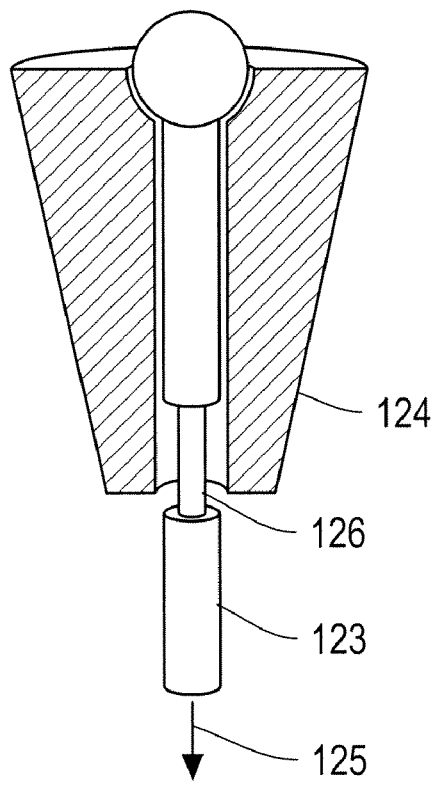
FIGS. 12a, 12b, and 12c show schematically an exemplary embodiment of an actuator with a pulling wire having a rated break point according to the invention.
Figure 12B:
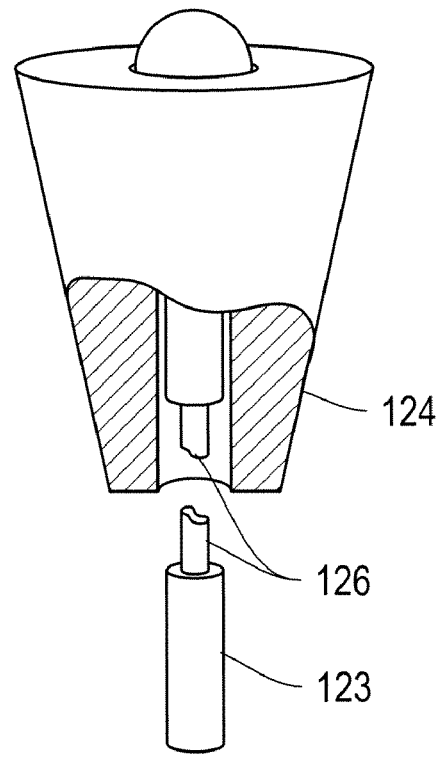

FIGS. 12a and 12b illustrate an exemplary detachment mode for a pulling wire 123 from a wedge-shaped locking element 124. The distal end of pulling wire 123 is held captive in a recess on locking element 124 and includes a section 126 on pulling wire 123 with a reduced diameter to provide a rated break point. After the wedge-shaped locking element 124 is drawn into the locking tube (not shown), the operator continues to pull downward on pulling wire 123 in the direction of arrow 125, separating the pulling wire 123 from the locking element 124 at the rated break point 126. The proximal end of pulling wire 123 can then be withdrawn from the body lumen.

Figure 12C:
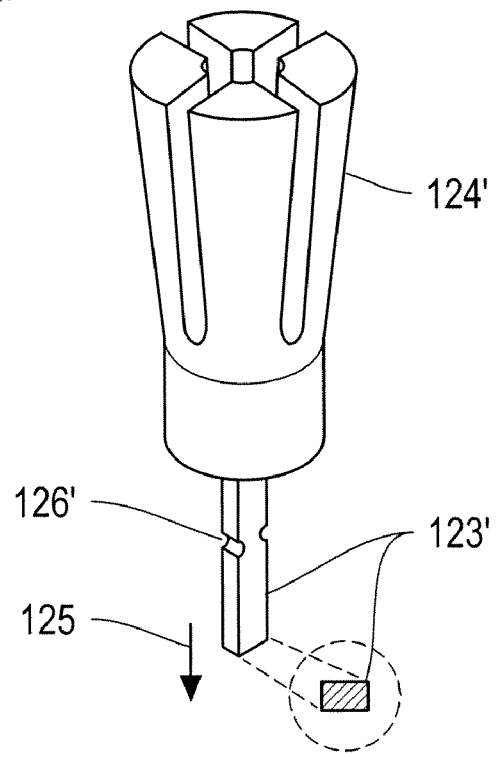

The embodiment illustrated in FIG. 12c is similar to that of FIGS. 12a and 12b, with the exception that the pulling wire 123' attached to locking element 124' has a rectangular cross-section (see insert) with lateral recesses 126' defining the rated break point.

Figure 13:
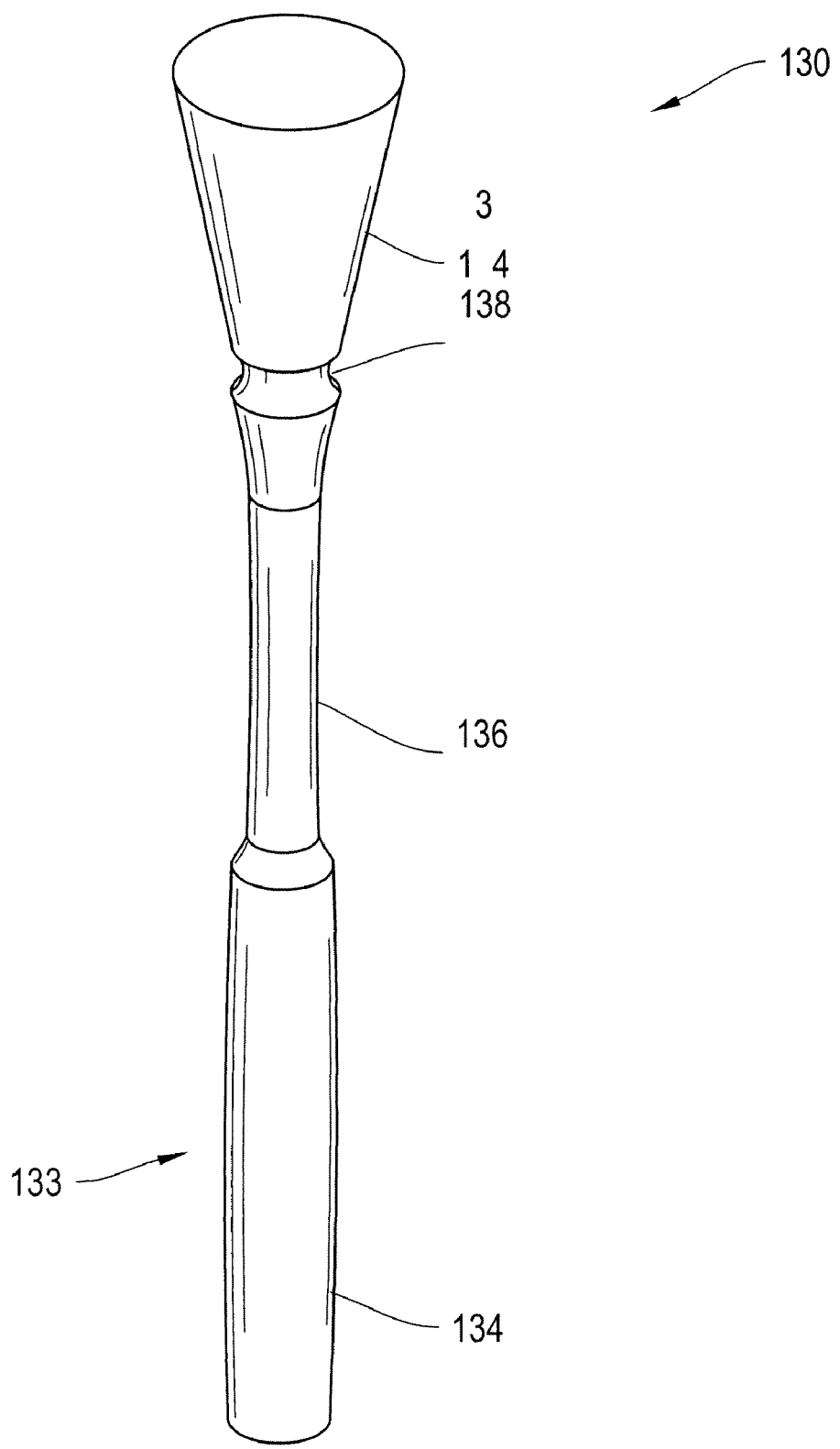
FIG. 13 shows schematically an exemplary embodiment of a locking element and an actuator formed as a single unit.

In another embodiment shown in FIG. 13, the locking element 134 and the user-activated actuator (pulling wire) 133 are formed as a single unit 130. In this embodiment, pulling wire 133 may include several sections of different thickness. For example, the proximal section 134 may have the greatest diameter, for example, 0.22 mm. The middle section 136 may have an intermediate diameter of about 0.15 mm, whereas the distal thin section 138 may have the smallest diameter of about 0.1 mm, defining the rated break point. This section is severed following locking onto the guidewire. The specified diameters and the depicted shape are provided by way of example for guidance only, and are not intended to be limiting, but only to illustrate a feature of the illustrated embodiment.

Figure 14:
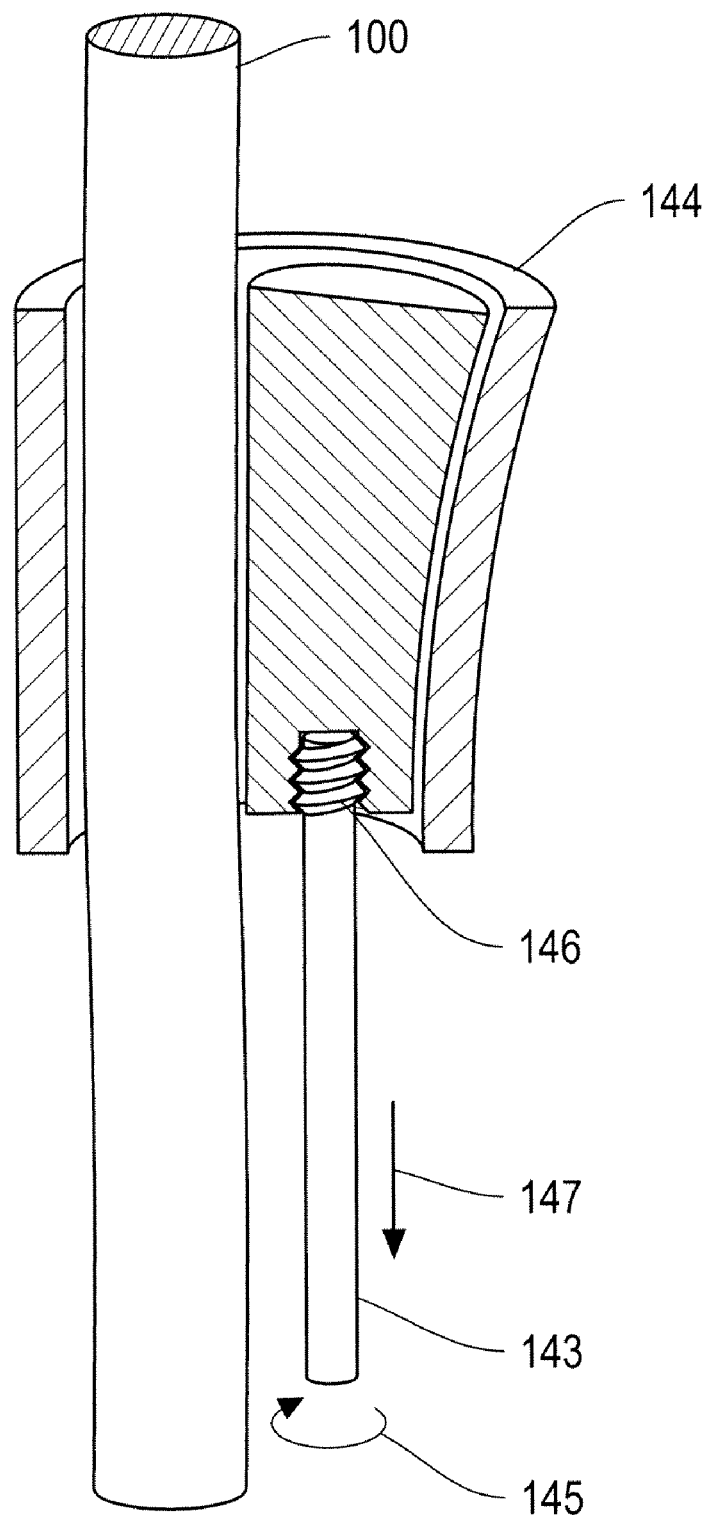
FIG. 14 shows schematically an exemplary embodiment of an actuator with a screw connection according to the invention.

Referring now to FIG. 14, the pulling wire 143 can be detached from the locking element 144 by a rotary motion 145 instead of by pulling the pulling wire in the proximal direction, as described in the previous examples. The pulling wire 143 includes at its distal end a threaded coupling 146 which engages with a corresponding threaded bore in locking element 144. The pulling wire 143 is pulled out of the body lumen after detachment from the locking element 144 in the direction of arrow 147.

Figure 15:
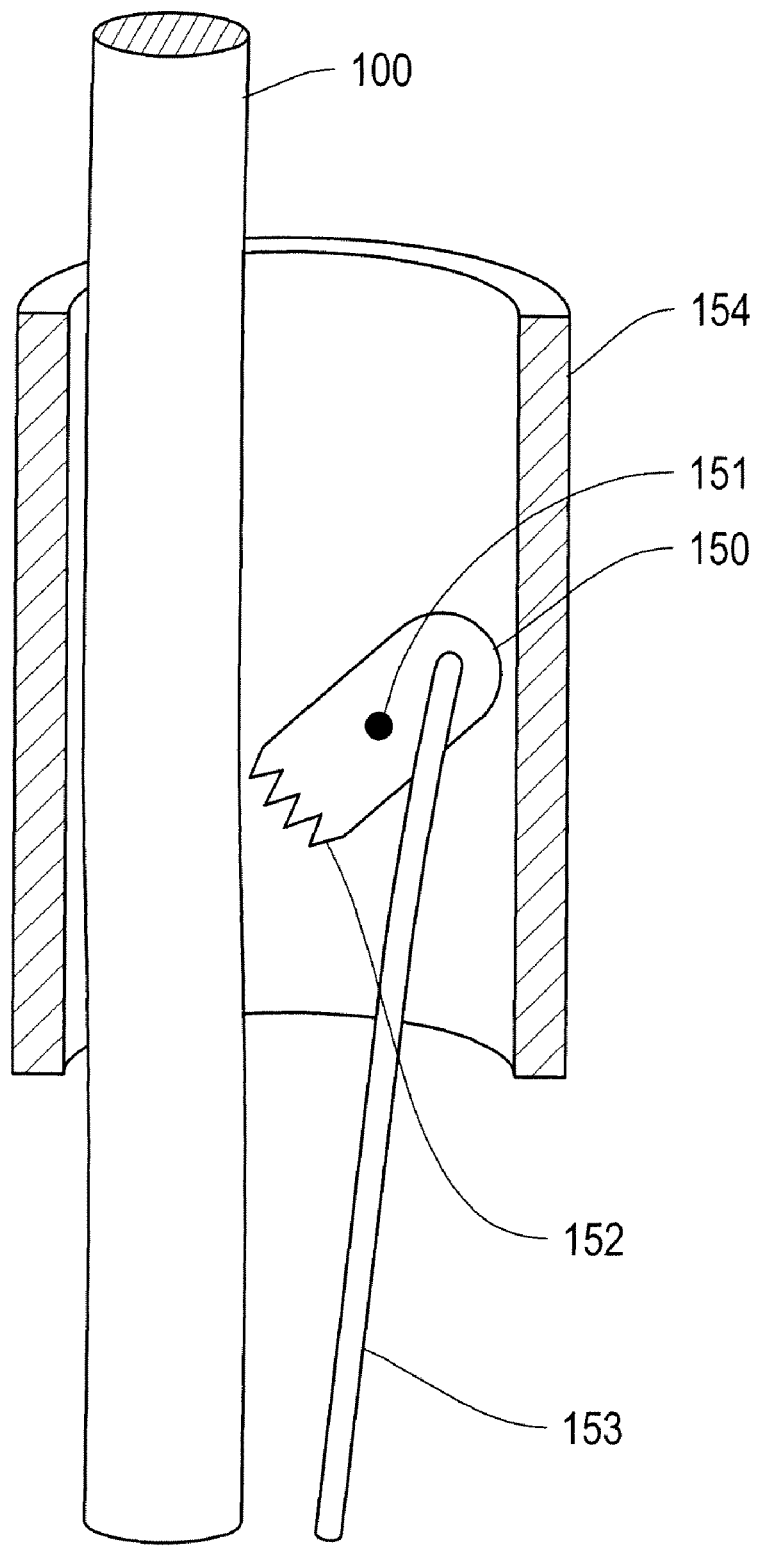
FIG. 15 shows schematically an exemplary embodiment of a cam-shaped locking element according to the invention.

FIG. 15 represents yet another embodiment for a locking element of the guidewire stop. In the illustrated embodiment, a cam element 150, optionally including one or more teeth 152, is configured for inward rotation about a pivot axis 151 inside a locking tube 154 when pulling wire 153 is pulled proximally. As element 150 rotates inward, a frictional holding force is applied on guidewire 100. In this embodiment, locking tube 154 provides support for the rotation of cam element 150, so that the length of locking tube 154 can be reduced compared to the previously described embodiments.

Figure 16A:
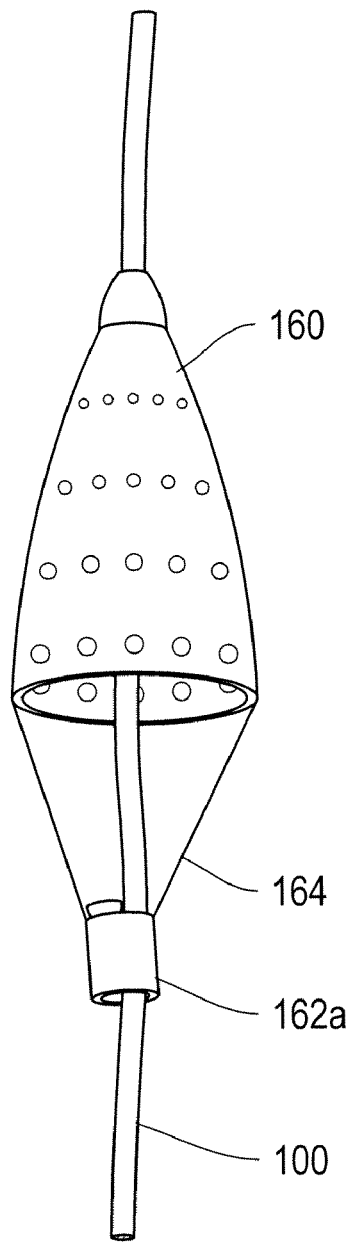
FIGS. 16a-16c illustrate schematically different placement of a guidewire stop cooperating with an embolic filter deployed over a guidewire.
Figure 16B:
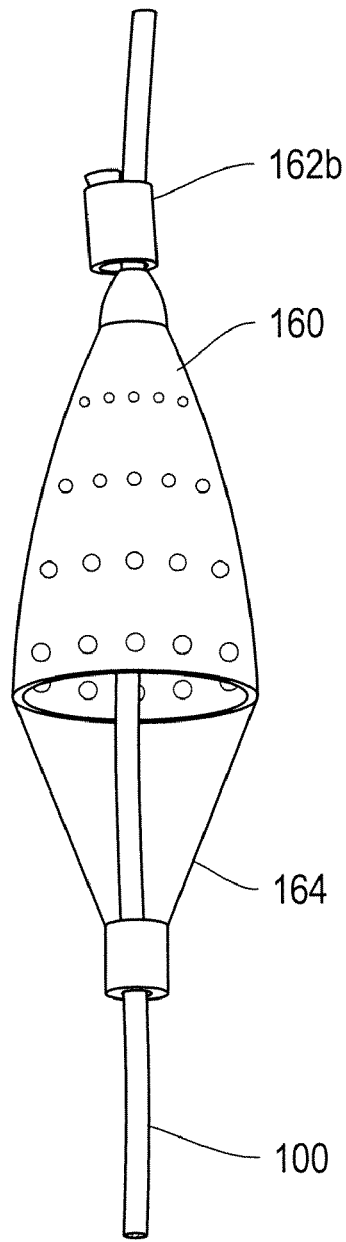
Figure 16C:
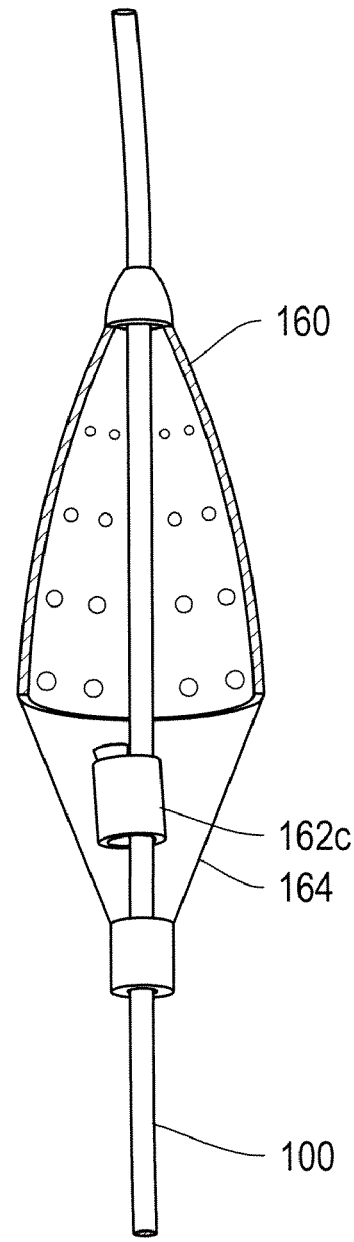

FIGS. 16a-16c illustrate various embodiments of locations of a guidewire stop on a guidewire useful for positioning a medical device, in the illustrated example an embolic protection filter 160, relative to a guidewire stop 162a, 162b, 162c. In one embodiment, illustrated in FIG. 16a, the filter 160 may be positioned distal to the guidewire stop 162a. Filters generally include a filter frame 164 attached to a sleeve which is slideably disposed about guidewire 100. The filter frame 164 may be affixed to the locking tube the guidewire stop 162a, as shown in more detail in FIG. 17. The filter frame and filter are not part of the present invention and will therefore not be described further.

In another embodiment depicted in FIG. 16b, a guidewire stop 162b is disposed distal of filter 160, but is not connected to the filter 160. The guidewire stop 162b is first locked onto the guidewire 100 at the desired location, for example under fluoroscopic observation, with the filter being advanced over the guidewire 100 to the guidewire stop 162b. The filter may be able to be retracted proximally along the guidewire 100 while leaving guidewire stop 162a in place, and may also rotate relative to guidewire 100.

Guidewire stop 162c may also be mounted on guidewire 100 between the distal and proximal ends of filter 160 as illustrated in FIG. 16c. In this embodiment, the filter may "float" with respect to the guidewire stop 162c, i.e., the filter 160 is able to move longitudinally along guidewire 100 over a distance defined approximately by the spacing between the proximal and distal ends of filter 160, and may also be able to rotate about the guidewire 100. It will be appreciated that these different options may be readily applied to medical devices other than embolic filters.

Figure 17:
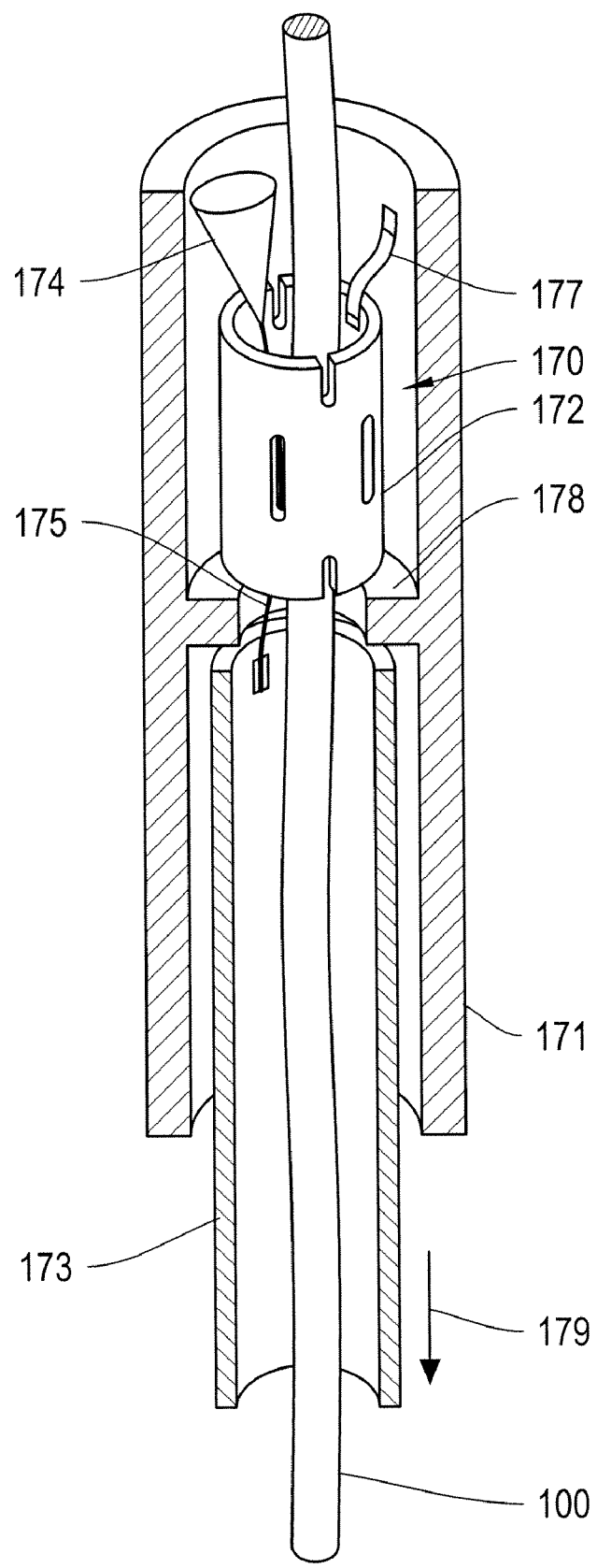
FIG. 17 shows in more detail a guidewire stop according to the invention configured for attachment of a medical device.

FIG. 17 illustrates in a more detailed partial cross-sectional view a guidewire stop 170 with a locking tube 172, shown here in the embodiment depicted in FIG. 11c, and a frame member 177 of a medical device, such as the embolic filter 160 of FIG. 16a, affixed to the locking tube 172. Also shown is a section of a delivery catheter 171 which may house the filter in the collapsed configuration and which includes an interior shoulder 178 which proximally supports the locking tube 172. A wedge-shaped locking element 174 is connected to a pulling wire or filament 175 which may be welded to an actuation tube 173. In alternative embodiments, the actuation tube 173 may be omitted and the pulling wire 175 may continue proximally and include a rated break point, as described above. As mentioned before, an actuating tube 173 may be used instead of or in conjunction with a wire to impart rotational motion.

In operation, a user pulls the actuation tube 173 in a direction indicated by arrow 179, thereby drawing the wedge-shaped locking element 174 into locking tube 172 and locking the guidewire stop 170 on guidewire 100 by friction. Continued pulling on actuation tube 173 severs the filament 175, allowing the actuation tube 173 to be withdrawn in the proximal direction 179.

After a procedure, the filter can be collapsed and withdrawn from the treatment site using a removal catheter (not shown).

While embodiments of the present invention have been described with reference to an embolic filter, it will be appreciated that the lock of the present invention may be employed with any medical device that is designed to be introduced into a body lumen through the use of a guidewire. Medical devices, such as, but not limited to, urological, neurological, or cardiological devices, may be implanted temporarily or permanently into a body lumen, for example, via a transcatheter procedure. The guidewire stop of the present invention provides a unique solution for the positioning and optionally locking such devices on bare guidewires.

While the invention is receptive to various modifications, and alternative forms, specific examples thereof have been shown in the drawings and are herein described in detail. It should be understood, however, that the invention is not limited to the particular forms or methods disclosed, but to the contrary, the invention is meant to cover all modifications, equivalents, and alternatives falling with the spirit and scope of the appended claims.

The invention claimed is:

1. An actuatable guidewire stop configured to limit movement of an intravascular device relative to a guidewire having a longitudinal direction, comprising:
   the guidewire;
   a locking tube disposed about the guidewire and having a locked configuration, wherein the locking tube is prevented from movement relative to the guidewire, and an unlocked configuration, wherein the locking tube is moveable relative to the guidewire;
   a tapered locking element having a first end portion constructed as a tip facing the locking tube and a second end portion having a radial dimension sufficiently large to urge the guidewire against an interior wall of the locking tube in the locked configuration, said tapered locking element independently moveable relative to both the guidewire and the locking tube in the unlocked configuration; and
   an actuator connected to the first end portion of the locking element, wherein upon actuation, the actuator moves the locking element in the longitudinal direction into a radial space between the locking tube and the guidewire and presses the guidewire against a portion of the interior wall of the locking tube that is not in contact with the tapered locking element, thereby placing the locking tube in the locked configuration.

2. The guidewire stop according to claim 1, wherein the locking tube comprises a resilient material.

3. The guidewire stop according to claim 1, wherein the locking tube has one of a grooved, spiral and multifilar structure.

4. The guidewire stop according to claim 1, wherein the tapered locking element is wedge-shaped.

5. The guidewire stop according to claim 1, wherein the tapered locking element comprises at least one friction-generating surface providing frictional engagement between the tapered locking element and at least one of the guidewire and the locking tube.

6. The guidewire stop according to claim 4, wherein the tapered member comprises a helical spring.

7. The guidewire stop according to claim 4, wherein the tapered member is configured as a wedge having a recess for receiving the guidewire.

8. The guidewire stop according to claim 1, wherein the actuator comprises a pulling wire having a rated break point.

9. The guidewire stop according to claim 1, wherein the actuator is operatively coupled to a tip portion of the tapered member by a separable screw connection.

10. The guidewire stop according to claim 1, wherein the locking element is moved into frictional engagement with at least the guidewire by a rotary movement of the actuator.

11. The guidewire stop according to claim 1, wherein the locking element and the actuator are formed as an integral unit.

12. The guidewire stop according to claim 1, wherein the actuator comprises a pulling wire extending in the longitudinal direction.

13. The guidewire stop according to claim 12, wherein the pulling wire has a rated break point.

14. The guidewire stop according to claim 12, wherein the pulling wire separates from the locking element when a pulling force applied longitudinally in a proximal direction exceeds a predetermined value.

15. The guidewire stop according to claim 1, wherein the tapered locking element and the actuator are formed as an integral unit.

16. An intravascular treatment device having a guidewire stop configured to limit movement of an intravascular device relative to a guidewire having a longitudinal direction, the guidewire stop comprising:
the guidewire;
a locking tube disposed about the guidewire and having a locked configuration, wherein the locking tube is prevented from movement relative to the guidewire, and an unlocked configuration, wherein the locking tube is moveable relative to the guidewire;
a tapered locking element having a first end portion constructed as a tip facing the locking tube and a second end portion having a radial dimension sufficiently large to urge the guidewire against an interior wall of the locking tube in the locked configuration, said tapered locking element independently moveable relative to both the guidewire and the locking tube in the unlocked configuration; and
an actuator connected to the first end portion of the locking element, wherein upon actuation, the actuator moves the locking element in the longitudinal direction into a radial space between the locking tube and the guidewire and presses the guidewire against a portion of the interior wall of the locking tube that is not in contact with the tapered locking element, thereby placing the locking tube in the locked configuration.

17. The device of claim 16, wherein the device is attached to the locking tube.

18. The device of claim 16, wherein the locking element comprises a wedge-shaped member and the actuator comprises a pulling wire, wherein the pulling wire separates from the locking element when a pulling force applied longitudinally in a proximal direction exceeds a predetermined value.

19. The device of claim 18, wherein the locking element and the pulling wire are formed as an integral unit.

20. The device of claim 16, wherein the device comprises an embolic filter.

21. A method for securing a guidewire stop along a length of a guidewire having a substantially uniform diameter and defining a longitudinal direction, the guidewire stop comprising a locking tube disposed about the guidewire and having a locked configuration, wherein the locking tube is prevented from movement relative to the guidewire, and an unlocked configuration, wherein the locking tube is moveable relative to the guidewire, a tapered locking element having a first end portion constructed as a tip facing the locking tube and a second end portion having a radial dimension sufficiently large to urge the guidewire against an interior wall of the locking tube in the locked configuration, said tapered locking element independently moveable relative to both the guidewire and the locking tube in the unlocked configuration; and an actuator connected to the first end portion of the locking element, the method comprising the steps of:
with a catheter, advancing the guidewire stop along the guidewire to a desired location;
actuating the actuator in the longitudinal direction so as to draw the locking element into a radial space between the locking tube and the guidewire, thereby pressing the guidewire against a portion of the interior wall of the locking tube that is not in contact with the tapered locking element, and
placing the locking element in the locked configuration;
detaching the actuator from the locking element; and
withdrawing the actuator in a proximal direction of the guidewire.

22. The method of claim 21, wherein the actuator comprises a pulling wire, and the step of detaching includes pulling the pulling wire in the proximal direction.

23. The method of claim 21, wherein the actuator threadingly engages the locking element, and the step of detaching includes rotating the actuator relative to the locking element.

* * * * *